US012629528B1

(12) United States Patent
Schobben et al.

(10) Patent No.: US 12,629,528 B1
(45) Date of Patent: May 19, 2026

(54) TEMPLATE FOR PLANNING A PLACEMENT OF ONE OR MORE PORTIONS OF A MEDICAL DEVICE

(71) Applicant: Salvia BioElectronics B.V., Eindhoven (NL)

(72) Inventors: Daniel Willem Elisabeth Schobben, Eindhoven (NL); Tom Delaey, Waalre (NL); Stijn Willem Boere, Eindhoven (NL); Wouter Harry Jacinth Rensen, Nuenen (NL)

(73) Assignee: Salvia BioElectronics B.V., Eindhoven (NL)

( * ) Notice: Subject to any disclaimer, the term of this patent is extended or adjusted under 35 U.S.C. 154(b) by 0 days.

(21) Appl. No.: 19/054,385

(22) Filed: Feb. 14, 2025

(51) Int. Cl.
*A61B 90/10* (2016.01)
*A61N 1/372* (2006.01)

(52) U.S. Cl.
CPC .................................... *A61N 1/372* (2013.01)

(58) Field of Classification Search
CPC .. A61N 1/0502; A61N 1/0504; A61N 1/0539; A61N 1/36017; A61B 90/10
See application file for complete search history.

(56) References Cited

U.S. PATENT DOCUMENTS

2009/0306652 A1* 12/2009 Buysse ............. A61B 18/1206
606/41

* cited by examiner

*Primary Examiner* — Alyssa M Alter
(74) *Attorney, Agent, or Firm* — Fresh IP PLC; Clifford D. Hyra; Aubrey Y. Chen

(57) ABSTRACT

A medical template is provided comprising one or more template portions corresponding to one or more device portions, with a first template face 121, arranged to be placed adjacent to one or more outer skin portions at least partially comprised in a curved skin plane 590; the first template face 121 being arranged to extend & curve longitudinally in a curved template plane 190, wherein the curved template plane 190 is arranged to be parallel to the curved skin plane 590. The medical template can comprise mechanically-resistive regions 130 arranged to resist transverse curvature of the first template face 121 such that at least a portion of the one or more mechanically-resistive regions deviates from the curved template plane 590. The medical template can also comprise one or more alignment marks 143, 183 offset to a degree corresponding to an implantation depth of a corresponding portion of the one or more device portions.

24 Claims, 11 Drawing Sheets

TEMPLATE FOR PLANNING A PLACEMENT OF ONE OR MORE PORTIONS OF A MEDICAL DEVICE

FIELD

The present disclosure relates to a medical template for planning a placement of one or more device portions, wherein the one or more device portions are comprised in an associated device for neurostimulation, wherein the one or more device portions are arranged to be at least partially implantable subcutaneously.

BACKGROUND

Health and wellness professionals often use templates or planning tools to mark the skin when planning a subsequent procedure, such as procedures with one or more cosmetic and/or medical steps.

These templates can be tedious to use. Common issues include: difficult placement and fixation of the template by one person, unclear marks and markings, unclear placement tolerances, unclear incision positions, and no warning of possible physical interference between the procedure being planned and other subsequent procedures or other devices.

These issues can cause errors during the subsequent procedure. These issues can cause serious complications during a subsequent procedure including one or more invasive steps, such as a surgical step.

The human body is controlled by patterns of electrical impulses transmitted through nerve fibers. In case of a chronic neurological disease, these electrical patterns can be affected. As an example, people can suffer from chronic migraines, pain, or mental disorders, among others. A migraine can affect electrical impulses in the brain. Bioelectronic devices can use mild electrical impulses to influence nerve activity (for neurostimulation), and potentially address the issues in the electrical patterns. Bioelectronic devices can be placed against a portion of outer skin to provide electrical impulses for various cosmetic and/or therapeutic purposes, such as transcutaneous electric nerve stimulation (TENS) and/or electrical muscle stimulation (EMS).

For example, to place an implanted neurostimulation system for those suffering from migraines, surgical incisions are required to create subcutaneous tunnels for lead and/or device placement. Such electrical impulses must be provided at predetermined and/or measured positions subcutaneously using suitable electrodes. Incorrect placement or partially incorrect placement can cause the associated device to work incorrectly, and can require additional surgical steps to correct the placement.

SUMMARY

To this end, in some embodiments the medical template comprises:

one or more template portions corresponding to the one or more device portions, the one or more template portions comprising a first template face, arranged to be placed adjacent to one or more outer skin portions of one or more body parts;

wherein the one or more outer skin portions are at least partially comprised in a curved skin plane;

wherein the first template face is arranged to extend longitudinally and to allow longitudinal curvature such that the first template face is mostly longitudinally comprised in a curved template plane;

wherein the curved template plane is arranged to be parallel to the curved skin plane;

wherein the medical template further comprises one or more alignment marks arranged to indicate one or more alignment axes and/or tolerances of placement; and wherein one or more positions and/or one or more extents of the one or more alignment marks is offset to a degree corresponding to an implantation depth of a corresponding portion of the one or more device portions.

The medical template according to this disclosure provides a higher degree of placement accuracy for one or more incisions and/or one or more electrodes by offsetting one or more positions and/or one or more extents of one or more alignment marks to a degree corresponding to an implantation depth of a corresponding portion of the one or more device portions. This is particularly advantageous if the one or more outer skin portions are curved, such as on a portion a head, a skull, a forehead, a brow, a temple region, or any combination thereof. This is especially advantageous for devices comprising one or more electrodes because transmission of electrical impulses can be partially reduced due to misalignment, and can sometimes produce an insufficient stimulus.

Optionally, the one or more positions and/or one or more extents of the one or more alignment marks are arranged to be offset in one or more longitudinal directions, in one or more transverse directions, or any combination thereof.

Optionally, the medical template is a surgical template.

Optionally, the medical template further comprises one or more incision marks, arranged to indicate one or more incision points and/or arranged to indicate one or more tolerances of incision.

Optionally, the medical template further comprises one or more incision marks, arranged to indicate one or more suitable directions for one or more incisions.

Optionally, the one or more body parts comprise at least a portion of a head, of a forehead, of a brow, of a temple region, or any combination thereof.

Optionally, the first template face is arranged to resist transverse curvature such that the first template face is transversely partially comprised in the curved template plane;

wherein the medical template further comprises one or more mechanically-resistive regions arranged to mechanically resist transverse curvature of the first template face such that at least a portion of the one or more mechanically-resistive regions deviates from the curved template plane.

Optionally, the medical template further comprises one or more indicator regions, arranged to indicate one or more deviations of the first template face from the curved template plane.

Optionally, the one or more indicator regions are arranged to indicate one or more deviations of the first template face in one or more longitudinal curvatures, in one or more transverse curvatures, or any combination thereof.

Additionally or alternatively, the one or more indicator regions are provided adjacent to a longitudinal extent, adjacent to a transverse extent, or any combination thereof.

Optionally, the medical template further comprises one or more attachment positions, and the medical template further comprises one or more elastic cords attached to the one or more attachment positions, wherein the one or more elastic cords are arranged to increase the area of the first template face comprised in the curved template plane.

Optionally, the one or more elastic cords are arranged to retain the medical template against at least a portion of the one or more body parts.

Additionally or alternatively, the one or more elastic cords are arranged to allow placement by one person.

For example, the one or more elastic cords can be fixed at both ends of the medical template. The stretch of the one or more elastic cords is arranged to be sufficient to allow placement, and the elasticity is arranged to be enough to hold the medical template in place.

Optionally, the medical template further comprises one or more guard rail grooves, arranged to assist in drawing one or more planning lines on one or more outer skin portions.

Optionally, the medical template further comprises one or more bumper regions, arranged to indicate a proximity to one or more further associated devices to be placed.

Optionally, the medical template further comprises one or more magnets, arranged to test a placement compatibility with one or more peripherals arranged to be attached to the associated device.

Optionally, the medical template further comprises one or more portions of a cardboard, a printed cardboard, a plastic, or any combination thereof.

Optionally, the medical template further comprises a dummy device of the associated device, wherein the dummy device comprises one or more positions, one or more extents, one or more marks, or any combination thereof, corresponding to a portion of the one or more device portions.

Use of a dummy device is advantageous because a real device does not need to be used and discarded after planning.

Optionally, the dummy device comprises one or more positions and/or one or more extents offset to a degree corresponding to an implantation depth of a corresponding portion of the one or more device portions.

Use of an offset dummy device is advantageous because using a real device does not make it easy to apply an offset that anticipates an implantation depth.

The present disclosure further relates to a medical template for planning a placement of one or more device portions, wherein the one or more device portions are comprised in an associated device for neurostimulation, wherein the one or more device portions are arranged to be placed on one or more body parts, in one or more body parts, or any combination thereof.

To this end, the medical template comprises one or more template portions corresponding to the one or more device portions, the one or more template portions comprising a first template face, arranged to be placed adjacent to one or more outer skin portions of one or more body parts;

wherein the one or more outer skin portions are at least partially comprised in a curved skin plane;

wherein the first template face is arranged to extend longitudinally and to allow longitudinal curvature such that the first template face is mostly longitudinally comprised in a curved template plane;

wherein the first template face is arranged to resist transverse curvature such that the first template face is transversely partially comprised in the curved template plane;

wherein the curved template plane is arranged to be parallel to the curved skin plane; and wherein the medical template further comprises one or more mechanically-resistive regions arranged to mechanically resist transverse curvature of the first template face such that at least a portion of the one or more mechanically-resistive regions deviates from the curved template plane.

The medical template according to this disclosure provides a higher degree of placement accuracy for one or more incisions and/or one or more electrodes by at least partially keeping the template parallel to the skin. This is particularly advantageous if the one or more outer skin portions are curved, such as on a portion a head, a skull, a forehead, a brow, a temple region, or any combination thereof. Use of such a medical template allows a planner to determine advantageous positions for electrodes and/or incisions. In particular, a planner can mark advantageous positions which are still understandable when the patient is covered during a subsequent procedure.

This is especially advantageous for devices comprising a thin substrate, such as foil-based and film-based bioelectronic devices, where the bending curvature of the substrate can be misaligned with respect to the local curvature of the adjacent body parts, such as a head or skull. This misalignment can cause local deviations of the foil, such as buckling, which is problematic because transmission of electrical impulses from the electrode to the skin can be reduced, electrode position can be incorrect, and the thin substrate can cut into surrounding tissues. If a portion of the thin substrate is implanted with buckling, the thin substrate can sometimes pierce an outer layer of skin.

In addition, using the template as disclosed herein, the planner can more often avoid the conventional solution requiring an implantable portion to be placed rigidly against a resistant anatomical structure, such as a portion of a skull, to reduce a risk of in-plane rotation or torsion of the implantable portion.

Optionally, the medical template further comprises one or more indicator regions arranged to indicate one or more deviations of the first template face from the curved template plane.

Optionally, the one or more indicator regions are arranged to indicate one or more deviations of the first template face in one or more longitudinal curvatures, in one or more transverse curvatures, or any combination thereof.

Additionally or alternatively, the one or more indicator regions are provided adjacent to a longitudinal edge, adjacent to a transverse edge, or any combination thereof.

Optionally, the medical template is a surgical template.

Optionally, the one or more body parts comprise at least a portion of a head, of a forehead, of a brow, of a temple region, or any combination thereof.

Optionally, one or more device portions are arranged to be at least partially implantable.

Optionally, one or more device portions are arranged to be at least partially implantable subcutaneously.

Optionally, the medical template further comprises one or more attachment positions, and further comprises one or more elastic cords attached to the one or more attachment positions, wherein the one or more elastic cords are arranged to increase the area of the first template face comprised in the curved template plane.

Optionally, the one or more elastic cords are arranged to retain the medical template against at least a portion of the one or more body parts.

Additionally or alternatively, the one or more elastic cords are arranged to allow placement by one person.

Optionally, the medical template further comprises one or more guard rail grooves, arranged to assist in drawing one or more planning lines on one or more outer skin portions.

Optionally, the medical template further comprises one or more alignment marks, arranged to indicate one or more alignment axes and/or tolerances of placement.

Optionally, the medical template further comprises one or more incision marks, arranged to indicate one or more incision points and/or arranged to indicate one or more tolerances of incision.

Optionally, the medical template further comprises one or more incision marks, arranged to indicate one or more suitable directions for one or more incisions.

Optionally, the medical template further comprises one or more bumper regions, arranged to indicate a proximity to one or more further associated devices to be placed.

Optionally, the medical template further comprises one or more magnets, arranged to test a placement compatibility with one or more peripherals arranged to be attached to the associated device.

Optionally, the medical template further comprises one or more portions of a cardboard, a printed cardboard, a plastic, or any combination thereof.

Optionally, the medical template further comprises a dummy device of the associated device, wherein the dummy device comprises one or more positions, one or more extents, one or more marks, or any combination thereof, corresponding to a portion of the one or more device portions.

Optionally, the dummy device comprises one or more positions and/or one or more extents offset to a degree corresponding to an implantation depth of a corresponding portion of the one or more device portions.

BRIEF DESCRIPTION OF DRAWINGS

The disclosure will now be illustrated with reference to the example section below, and with reference to the drawing wherein.

DETAILED DESCRIPTION

Figure 1:
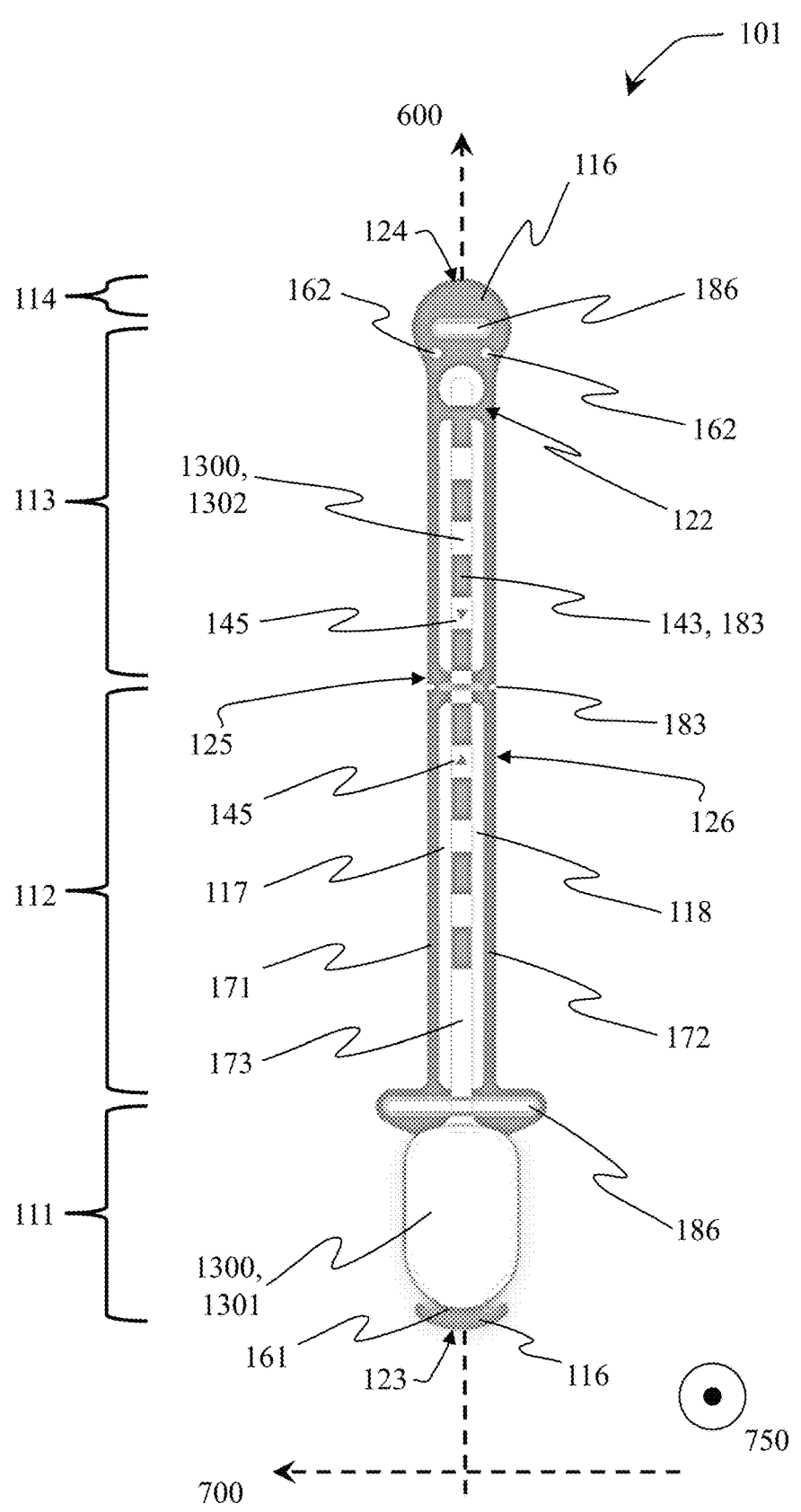
FIG. 1 is a first embodiment of a medical template.

Template portions are sections of a medical template that correspond to specific parts of a medical device. Each template portion includes a first template face designed to be placed next to the outer skin of a body part.

A curved skin plane refers to a natural curvature of the skin on a body part where a medical template is to be applied. The outer skin portions are at least partially included in this curved skin plane.

A first template face is a surface of a template portion that is intended to be placed adjacent to the skin. It is designed to extend in a longitudinal direction and to accommodate curvature, such that the first template face aligns with a curved template plane.

A curved template plane is an imaginary plane, parallel to a curved skin plane, representing a predetermined or intended placement of a template portion. If a portion of a first template face is comprised in a curved template plane, this portion of the first template face is arranged according to a predetermined or intended placement.

Longitudinal curvature is a curvature of an object or surface along its length. In the context of this disclosure, longitudinal curvature is arranged to allow a portion of a medical template to conform to a curved surface of skin along the length of the medical template. The primary orientation is longitudinal, but there can be some degree of flexibility or variation in one or more transverse directions.

Longitudinally comprised means that a portion of a longitudinal curvature is comprised in a curved template plane. Mostly longitudinally comprised means that a majority of a longitudinal curvature is comprised in a curved template plane, wherein mostly is more than 508, or more than 608, or more than 708, or more than 808, or more than 90%.

An alignment mark in an indicator on a medical template that show an alignment axis and/or a placement tolerance. Alignment marks are arranged to help position a medical template correctly on the body.

An offset alignment mark is an alignment mark with a position and/or extent which is adjusted to account for an implantation depth of a corresponding device portion, allowing a more accurate placement of a device portion within the body.

An indicator region is a specific area on a medical template arranged to signal or highlight a deviation from an intended placement or an alignment of the medical template on the body. An indicator region can be arranged to provide a visual and/or tactile feedback to a user about a degree of the conformity or non-conformity of a medical template to the body's surface. If a medical template is not properly aligned or buckles, an indicator region is arranged to show a deviation from an expected plane, alerting a user to adjust the medical template for a more accurate fit. An indicator region can be located adjacent to an edge of a medical template and/or along a specific axis. An indicator region can be arranged to respond to a longitudinal and/or a transverse deviation.

A guard rail is a specific area on a medical template arranged to at least partially define a guard rail groove. Additionally or alternatively, a guard rail can comprise one or more indicator regions.

A dummy device is a replica or model of a medical device used for planning and visualization purposes. A dummy device is arranged to mimic, for example, a size, a shape, a weight, or any combination thereof of an actual medical device to be used in a subsequent procedure. A dummy device can be non-functional, partially functional or fully functional. A dummy device can be an actual medical device which does not need to be sterilized and/or disinfected.

The medical templates as described herein are detailed medical tools designed to enhance the accurate placement of the associated devices. Each medical template comprises one or more portions directly correspond to one or more portions of the relevant device to be implanted. Each embodiment of the medical template provides varying degrees of guidance, from comprehensive templates with numerous markers to more simplified versions, catering to different cosmetic and/or medical steps, or to different types of associated device.

FIG. 1 depicts a first embodiment of a medical template 101 (or a first medical template) suitable for planning a subsequent procedure such as a placement of one or more device portions. The subsequent procedure can include one or more cosmetic and/or medical steps.

The one or more device portions are comprised in an associated device, wherein the associated device is arranged for providing and/or assisting with one or more cosmetic and/or therapeutic steps. The one or more device portions are arranged to be placed on one or more body parts (not depicted), in one or more body parts, or any combination thereof. For example, the associated device can be a bio- electronic device (or neurostimulator) arranged to provide one or more electrical impulses at predetermined and/or measured positions using one or more electrodes.

The first medical template 101 is suitable for planning a placement of one or more device portions on a user (not depicted) of the associated device. The user (or end user) can be, for example, a human or an animal.

During planning, a planner can use the first medical template 101 to plan a subsequent procedure. The planner can be, for example, a health and/or wellness professional, a nurse, a doctor, a surgeon, or another user of the associated device. Additionally or alternatively, the planner can also be the user of the associated device if the first medical template 101 is arranged for at least partial self-planning as described below.

So, before the subsequent procedure, the first medical template 101 is placed at the corresponding region of the body of the user where the associated device will be placed, such as a cranial region.

As depicted in FIG. 1, the first medical template 101 comprises: a substrate extending along a longitudinal axis 600 from a first longitudinal edge 123 to a second longitu- dinal edge 124, and further extending along a first transverse axis 700 from a first transverse edge 125 to a second transverse edge 126; and one or more template portions 111, 112, 113, 114. The first medical template 101 optionally comprises one or more alignment marks 143, 145. Addi- tionally or alternatively, the first medical template 101 comprises one or more incision marks 186.

In the example depicted in FIG. 1, the first medical template 101 optionally comprises a first template portion 111, a second template portion 112, a third template portion 113 and a fourth template portion 114, arranged adjacently along the longitudinal axis 600. The first template portion 111 is arranged at a proximal end (not labelled) of the first medical template 101. The fourth template portion 114 is arranged at a distal end (not labelled) of the first medical template 101.

The one or more template portions 111, 112, 113, 114 comprise a first template face (not depicted) arranged to be placed adjacent to one or more outer skin portions (not depicted) of the user. Optionally, the one or more template portions 111, 112, 113, 114 can comprise a second template face 122, on the opposite side of the substrate to the first template face. Optionally, the second template face 122 can comprise one or more marks, markers and/or labels. Option- ally the second template face 122 can be arranged to be visible during planning.

In the example depicted in FIG. 1, the first medical template 101 optionally comprises a dummy 1300 of the associated device (dummy device) to reduce the risk of inconsistencies between the dimensions and markings of the first medical template 101 and the associated device. The dummy 1300 is a representation of the associated device, used for visualization and measurement during the planning. The dummy 1300 also allows an estimate of any future undesirable interactions of the associated device with other peripherals the user could use, such as glasses. Optionally, a built-in magnet (not depicted) could be used test or align the dummy 1300 with external components of the associated device.

If the associated device is, for example, a neurostimulator, the dummy device 1300 can comprise a dummy pulse generator 1301 and/or one or more dummy electrodes 1302. The one or more dummy electrodes 1302 can represent the foil or conductor component of the associated device, assist- ing in the alignment of the one or more conductive elements. In the example depicted in FIG. 1, the first medical template 101 comprises one or more dummy electrodes 1302 with longitudinal alignment marks 143 and transverse alignment marks 183 indicating one or more positions of one or more electrodes comprised in the associated device, allowing a planner to accurately determine correct positions for the one or more electrodes using the first medical template 101.

In the example depicted in FIG. 1, the first template portion 111 extends from the proximal end of the first medical template 101 to an optional first transverse incision mark 186, with a transverse extent approximately parallel to the first transverse axis 700. The first transverse incision mark 186 provides a suitable means to allow the planner to mark one or more outer skin portions of the user with one or more positions of the first transverse incision mark 186. For example by providing a groove large enough to allow a marker to pass through. Additionally or alternatively, a desired direction of one or more incisions can also be marked, such as a transverse direction, a longitudinal direc- tion, or any combination thereof. In the example depicted in FIG. 1, the first transverse incision mark 186 is arranged to indicate a transverse direction by being extended along a first transverse axis 700, thereby indicating to a planner that an incision is to be marked and subsequently made in a first transverse direction 700.

In the example depicted in FIG. 1, the second template portion 112 extends from the optional first transverse inci- sion mark 186 to an optional transverse alignment mark 183, with a transverse extent approximately parallel to the first transverse axis 700. The transverse alignment mark 183 provides a suitable means to allow the planner to mark one or more outer skin portions of the user with one or more positions of the transverse alignment mark 183. For example by extending the transverse alignment mark 183 to one or more transverse edges 125, 126 of the first medical template 101 whereby a marker can be used at the edges. Optionally, the transverse alignment mark 183 can be used to define a center alignment.

In the example depicted in FIG. 1, the third template portion 113 extends from the optional transverse alignment mark 183 to the optional second transverse incision mark 186, with a transverse extent approximately parallel to the first transverse axis 700. The second transverse incision mark 186 provides a suitable means to allow the planner to mark one or more outer skin portions of the user with one or more positions of the second transverse incision mark 186. For example by providing a groove large enough to allow a marker to pass through. In the example depicted in FIG. 1, the second transverse incision mark 186 is arranged to indicate a transverse direction by being extended along a first transverse axis 700, thereby indicating to a planner that an incision is to be marked and subsequently made in a first transverse direction 700.

In the example depicted in FIG. 1, the fourth template portion 114 extends from the optional second transverse incision mark 186 to the distal end of the first medical template 101.

The first template face is arranged to be placed adjacent to one or more outer skin portions during planning, wherein the one or more outer skin portions are at least partially comprised in a curved skin plane. Skin portions are usually not completely flat, and are often curved or very curved, such as on a portion a head or skull.

The first template face is arranged to extend longitudinally along the longitudinal axis 600, and to allow longitudinal curvature such that the first template face is mostly longitudinally comprised in a curved template plane.

For example, by comprising one or more materials that are flexible enough to conform to the one or more outer skin portions. For example, the first medical template 101 can comprise one or more portions of a cardboard, a printed cardboard, a plastic, or any combination thereof. For example, by being thin enough to conform to the one or more outer skin portions. For example, by having an average thickness in the range 0.6 to 1.2 mm, or 0.8 to 1.0 mm. For example, manufacturing using 3D-printing with a one or more suitable plastics, such as ABS, PLA, PETG and/or nylon. For example, 15 to 25 layers of Loctite 3D MED413 of approximately 0.13 mm can be used, with an average Tensile Stress at Break of approx. 70 MPa, an average Young's Modulus of 1600 MPa, an average Elongation at Break of approx. 50%, and an average HDT at 0.455 MPa at 70° C. Preferably, the materials used should have a high degree of biocompatibility. One or more template portions that don not need to be curved can be thicker—for example 4 to 8 mm average thickness.

The first template face is further arranged with a transverse extent along the first transverse axis 700, and to resist transverse curvature such that the first template face is transversely partially comprised in the curved template plane. The curved template plane is arranged to be approximately parallel to the curved skin plane during planning.

The first medical template 101 comprises one or more mechanically-resistive regions arranged to mechanically resist transverse curvature of the first template face such that at least a portion of the one or more mechanically-resistive regions deviates from the curved template plane. The one or more mechanically-resistant regions are arranged to allow a degree of curvature in the longitudinal direction 600 sufficient to allows the first medical template 101 to longitudinally follow the curved skin plane, but also sufficient to resist a degree of curvature in a transverse direction 700.

For example, the first medical template 101 can comprise one or more portions being thick enough to resist conforming to the one or more outer skin portions.

For example, the first medical template 101 can comprise one or more grooves, extending longitudinally over at least a portion of one or more template parts 111, 112, 113, 114, whereby the substrate is separated into two or more longitudinal strips. During planning, if the first template face does not fully conform to the curved skin plane, the two or more longitudinal strips provide a degree of mechanical resistance such that one or more portions of each longitudinal strip can deviate to a different amount from the curved template plane.

In the example depicted in FIG. 1, the first medical template 101 optionally comprises a first guard rail groove 117 adjacent to the first transverse edge 125 of the first medical template 101, and optionally comprises a second guard rail groove 118 adjacent to the second transverse edge 126 of the first medical template 101. The first guard rail groove 117 and the second guard rail groove 118 extend longitudinally over at least a portion of the second template part 112, whereby the substrate is separated into three longitudinal strips—a first guard rail, a central substrate portion and a second guard rail.

Optionally, the first guard rail can comprise a first indicator region 171. Optionally, the second guard rail can comprise a second indicator region 172. Optionally, the central substrate portion can comprise a third indicator region 173. Optionally, the first medical template 101 can be arranged such that, during planning, if the first template face does not fully conform to the curve skin plane, the one or more of the three longitudinal strips provide a degree of mechanical resistance such that one or more indicator regions visibly deviate from the curved template plane, thereby alerting the planner that the template is not quite flat in the first transverse direction 700. These indicator regions can also be described as buckling indicators. One or more indicator regions can therefore be configured to identify portions where the first medical template 101 has buckled, and these portions directly correspond to portions of the associated device which should remain straight flat during placement. These indicator regions can also be described as torsion indicators.

Optionally, the first medical template 101 can comprise one or more attachment positions, and the first medical template 101 can further comprise one or more cords and/or ties attached to the one or more attachment positions. The one or more cords and/or ties can then be arranged to improve handling and/or fixation of the first medical template 101 as explained below in relation to FIG. 3. In the example depicted in FIG. 1, the first medical template 101 optionally comprises first attachment position 161 adjacent to the proximal end in the first template portion 111. In the example depicted in FIG. 1, the first medical template 101 optionally comprises two second attachment positions 162 adjacent to the distal end in the third template portion 113.

The first medical template 101 can optionally comprise one or more marking grooves, arranged to be large enough to allow a marker to pass through. Marking grooves can be used by the planner to draw one or more planning lines, such as an end of a lead or electrode array, aiding in alignment and/or placement during a subsequent procedure. For example, one or more portions of one or more guard rail grooves can be arranged as one or more marking grooves.

Optionally, one or more marks, markings and/or labels can be provided on the first medical template 101 to guide the planner to align the first medical template 101 correctly with respect to one or more anatomical features of the one or more body parts. Optionally, one or more marks, markings and/or labels can be provided on the second template face 122. Optionally, shading and/or color coding can be used to distinguish the functions of different parts and/or markings. Optionally, one or more areas may be provided for branding and/or critical instructions, such as a visible surface of the dummy pulse generator 1301.

Optionally, the first medical template 101 can comprise one or more bumper areas or bumper regions, arranged to indicate areas that should be kept free, thereby reducing the risk that two or more associated devices interfere with each other after placement. In the example depicted in FIG. 1, the first medical template 101 optionally comprises a first bumper region 116 at the proximal end in the first template portion 111. In the example depicted in FIG. 1, the first medical template 101 optionally comprises a second bumper region 116 at the distal end in the fourth template portion 114.

Optionally, the first medical template 101 can comprise one or more tolerance marks, arranged to indicate one or more tolerances or a margin of error allowed during the placement of the associated device. In the example depicted in FIG. 1, the first medical template 101 optionally comprises a first longitudinal tolerance mark 145 comprised in the second template portion 112, and a second longitudinal tolerance mark 145 comprised in the third template portion 113.

Figure 2:
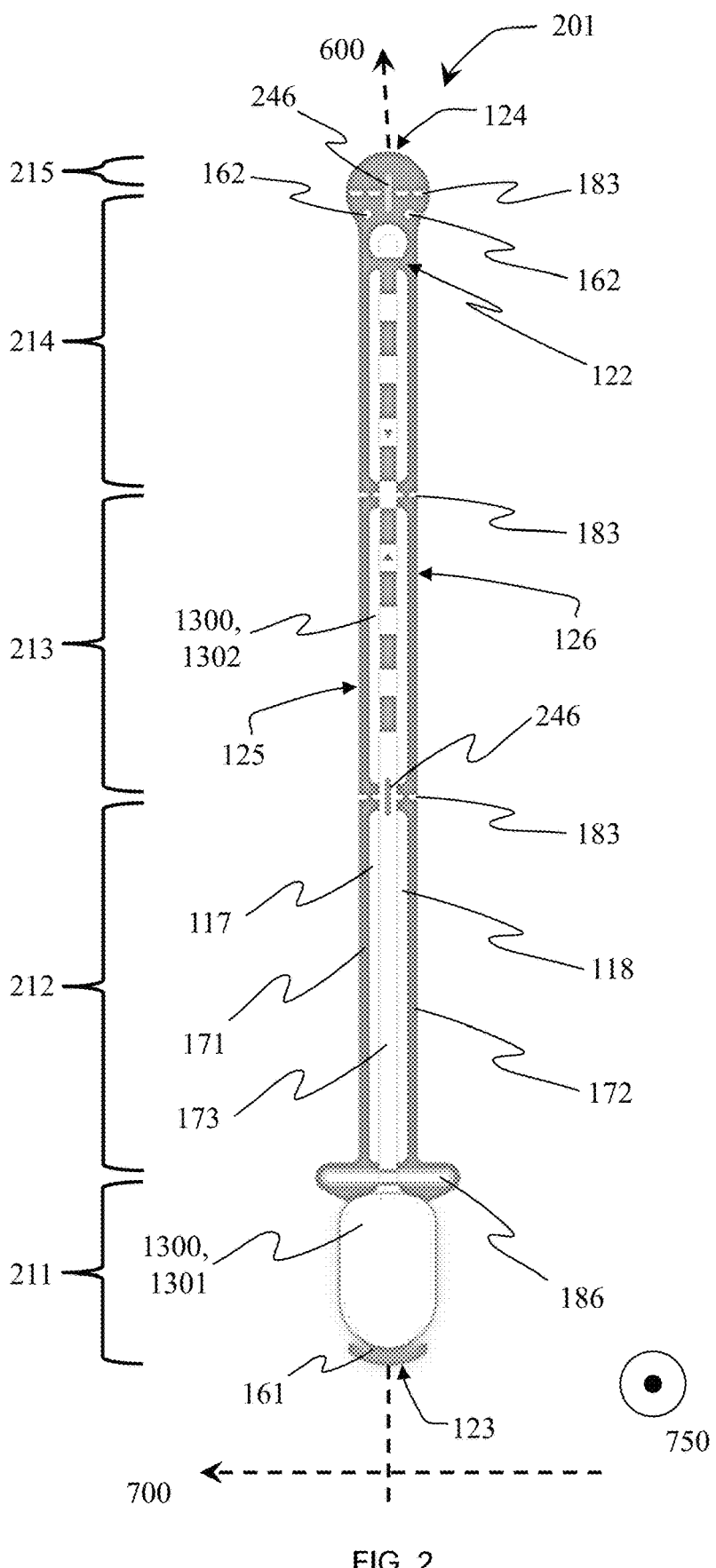
FIG. 2 is a second embodiment of a medical template.

FIG. 2 depicts a second embodiment of a medical template 201 (or a second medical template) suitable for planning a subsequent procedure such as a placement of one or more device portions. The second medical template 201 is the same as the first medical template 101 depicted in FIG. 1 except for the differences explained below.

The second medical template 201 differs by comprising a first template portion 211, a second template portion 212, a third template portion 213, a fourth template portion 214, and a fifth template portion 215, arranged adjacently along the longitudinal axis 600. These template portions 211, 212, 213, 214, 215 correspond respectively to a first device portion (not depicted), a second device portion (not depicted), a third device portion (not depicted), and a fourth device portion (not depicted). The one or more template portions of the second medical template 201 comprise a first template face which is arranged to be placed adjacent to one or more outer skin portions. In these examples, the first template portion 211, the second template portion 212, the third template portion 213, the fourth template portion 214, and the fifth template portion 215 are arranged to be placed adjacent to respectively a first outer skin portion 511, a second outer skin portion 512, a third outer skin portion 513, a fourth outer skin portion 514, and a fifth outer skin portion 515.

In the example depicted in FIG. 2, the first template portion 211 extends from the proximal end of the second medical template 201 to an optional first transverse incision mark 186, extending transversely approximately parallel to the first transverse axis 700. The first transverse incision mark 186 provides a suitable means to allow the planner to mark one or more outer skin portions of the user with one or more positions of the first transverse incision mark 186. For example by providing a groove large enough to allow a marker to pass through. Additionally or alternatively, a desired direction of one or more incisions can also be marked.

The second medical template 201 differs by the second template portion 212 extending from the optional first transverse incision mark 186 to an optional first transverse alignment mark 183, extending transversely approximately parallel to the first transverse axis 700. The first transverse alignment mark 183 provides a suitable means to allow the planner to mark one or more outer skin portions of the user with one or more positions of the first transverse alignment mark 183. For example by extending the first transverse alignment mark 183 to one or more transverse edges 125, 126 of the second medical template 201 whereby a marker can be used at the edges.

The second medical template 201 differs by the third template portion 213 extending from the optional first transverse alignment mark 183 to the optional second transverse alignment mark 183, extending transversely approximately parallel to the first transverse axis 700. The second transverse alignment mark 183 provides a suitable means to allow the planner to mark one or more outer skin portions of the user with one or more positions of the second transverse alignment mark 183. For example by extending the second transverse alignment mark 183 to one or more transverse edges 125, 126 of the second medical template 201 whereby a marker can be used at the edges.

The second medical template 201 differs by the fourth template portion 214 extending from the optional second transverse alignment mark 183 to the optional third transverse alignment mark 183, extending transversely approximately parallel to the first transverse axis 700. The third transverse alignment mark 183 provides a suitable means to allow the planner to mark one or more outer skin portions of the user with one or more positions of the third transverse alignment mark 183. For example by extending the third transverse alignment mark 183 to one or more transverse edges 125, 126 of the second medical template 201 whereby a marker can be used at the edges.

The second medical template 201 differs by the fifth template portion 115 extending from the optional third transverse alignment mark 183 to the distal end of the second medical template 101.

The second medical template 201 differs by comprising an optional first longitudinal incision mark 246 and an optional second longitudinal incision mark 246, each extending longitudinally approximately parallel to the longitudinal axis 600. Each longitudinal incision mark 246 provides a suitable means to allow the planner to mark one or more outer skin portions of the user with one or more positions of the longitudinal incision mark 246. For example, by providing a groove large enough to allow a marker to pass through. In the example depicted in FIG. 2, the first longitudinal incision mark 246 extends from the second template portion 212 to the third template portion 213, adjacent to the first transverse alignment mark 183. In the example depicted in FIG. 2, the second longitudinal incision mark 246 extends from the fourth template portion 214 to the fifth template portion 215, adjacent to the third transverse alignment mark 183. In the example depicted in FIG. 2, the first longitudinal incision mark 246 is arranged to indicate a longitudinal direction by being extended along a longitudinal axis 600, thereby indicating to a planner that an incision is to be marked and subsequently made in a longitudinal direction 600.

In the example depicted in FIG. 2, the second medical template 201 optionally comprises a first attachment position 161 adjacent to the proximal end in the first template portion 211. In the example depicted in FIG. 2, the second medical template 201 optionally comprises two second attachment positions 162 adjacent to the distal end in the fourth template portion 214.

Figure 3:
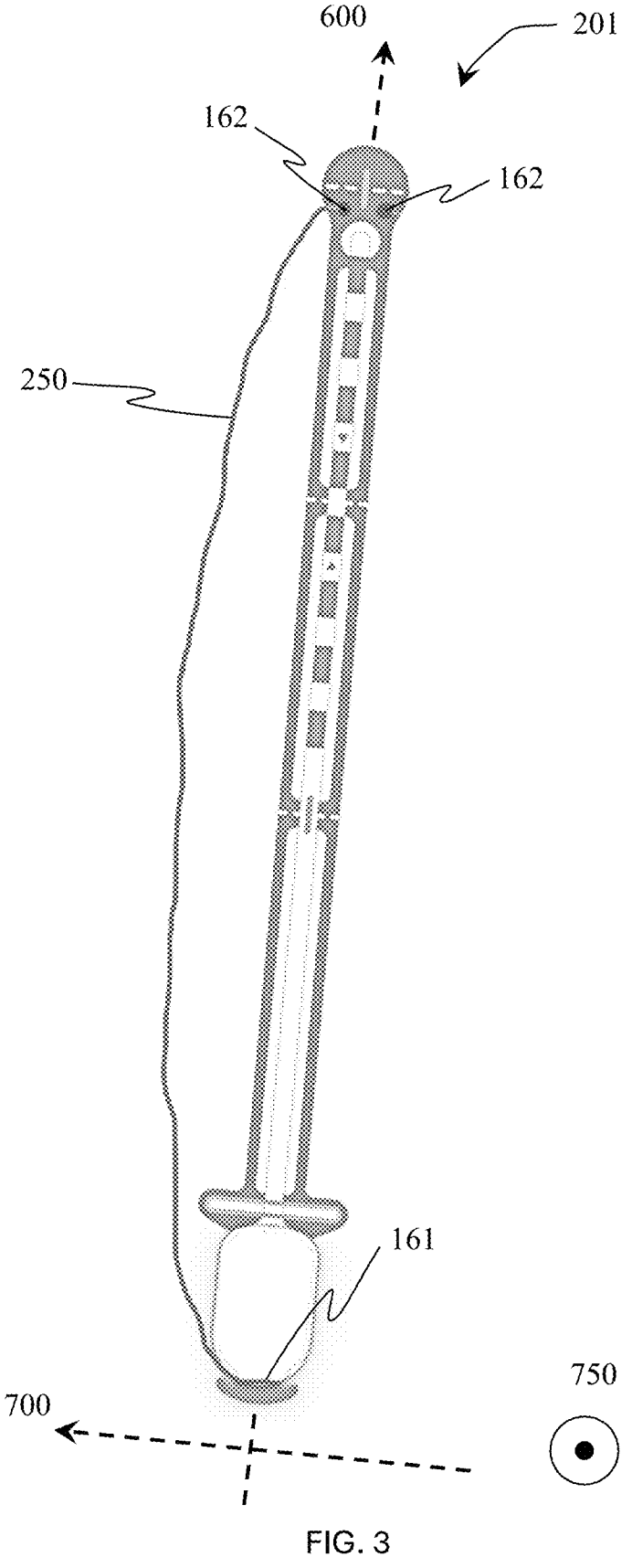
FIG. 3 is a further embodiment of a medical template.

FIG. 3 depicts the same medical template 201 as depicted in FIG. 2, but modified with the differences explained below. Optionally, the second medical template 201 can comprise one or more attachment positions, and the second medical template 201 can further comprise one or more cords and/or ties attached to the one or more attachment positions. The one or more cords and/or ties can then be arranged to improve handling and/or fixation of the second medical template 201. The one or more elastic cords can then be arranged to increase the area of the first template face comprised in the curved template plane by applying force to increase the level of conformance between the substrate of the second medical template 201 and the curved skin plane. In the example depicted in FIG. 2 and FIG. 3, the second medical template 201 optionally comprises a first attachment position 161 adjacent to the proximal end. In the example depicted in FIG. 2 and FIG. 3, the second medical template 201 optionally comprises two second attachment positions 162 adjacent to the distal end. The optional one or more attachment positions 161, 162 can be a slot, a groove, a recess, a protrusion, a hole, an aperture, or any combination thereof.

As depicted in FIG. 3, the modified second medical template 201 further comprises one or more elastic cords 250, such as a bungie-type cord, arranged to provide sufficient force to retain the second medical template 201 in position against at least a portion of the one or more outer skin portions (not depicted). The second medical template 201 as depicted is therefore arranged to improve the likelihood that the modified second medical template 201 remains in position after placement. This provides a more stable and more precise guide for subsequent medical procedures. This provides a further advantage if a subsequent procedure is more invasive, such as a procedure including one or more surgical steps.

The one or more elastic cords 250 can comprise any suitable elastic type. For example, one or more elastic beading/bracelet threads, can be used. For example, the one or more elastic cords 250 can comprise any suitable materials, such as spandex. For example, the one or more elastic cords can have a suitable average diameter, such as approximately 0.8 mm.

The one or more elastic cords 250 can have any suitable elastic length which allows the one or more elastic cords 250 to pass around the one or more body parts (not depicted), such as around a head. Optionally, the one or more elastic cords 250 can be arranged to have an adjustable length.

Optionally, the one or more elastic cords 250 can be arranged to facilitate placement by a single person by further increasing the force exerted such that the modified second medical template 201 can be held in place during planning using only one or two hands.

Optionally, the one or more elastic cords 250 can be attached to the modified second medical template 201 during planning and/or before planning. Optionally, the one or more elastic cords 250 can be pre-mounted during manufacturing. Optionally, the one or more elastic cords 250 can be more securely attached using one or more labels, stickers, glues, or any combination thereof.

FIGS. 4A to 4D collectively depict different views of a correctly-placed medical template as described herein. In these examples, the modified second medical template 201 as depicted in FIG. 3 is arranged to be placed on one or more body-parts 500 of a user. In these examples, the one or more body-parts 500 are one or more parts of the head of a user, illustrated schematically using a mannequin head. In these examples, the modified second medical template 201 is arranged to at least partially wrap around the head, with specific attention to at least a portion of a forehead, of a brow, of a temple region, or any combination thereof.

In these examples, the associated device (not depicted) is suitable for neurostimulation, for example a neurostimulator. Optionally, one or more device portions can be arranged to be at least partially implantable, for example subcutaneously.

The modified second medical template 201 comprises one or more elastic cords 250, such as a bungie-type cord, arranged to remain in position after placement. This provides a stable and precise guide for surgical procedures, because a higher degree of accuracy is required in planning the one or more incisions. A higher degree of accuracy is particularly advantageous if the associated-device (not depicted) is a neurostimulation implant, because the user will be using the associated-device for long periods during their daily lives.

Figure 4A:
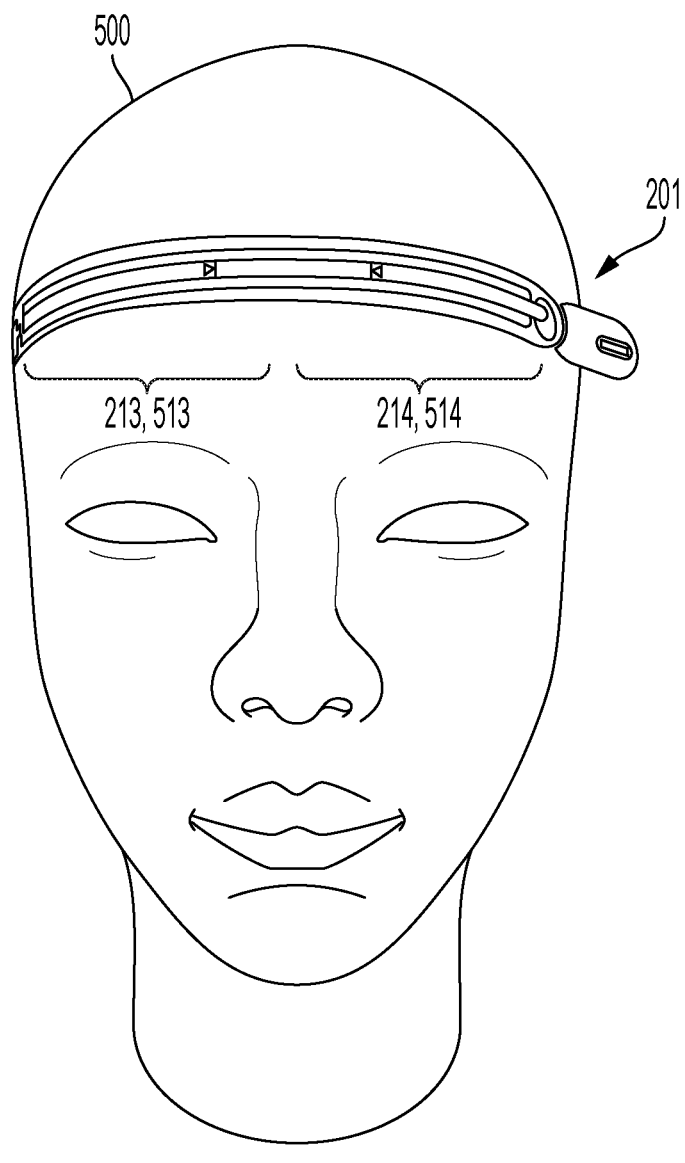
FIG. 4A is a front-view of a correctly-placed template.

FIG. 4A depicts a front-view of the modified second medical template 201 after correct placement. The front-view is the perspective that a planner sees if looking directly at the face of the user, or the view that a user sees if looking in a mirror or in a self-portrait during self-planning.

As depicted, the head of the user is depicted approximately vertical or upright. The modified second medical template 201 is positioned approximately horizontally across the forehead of the mannequin, wherein the third template portion 213 is adjacent to the third outer skin portion 513, and the fourth template portion 214 is adjacent to the fourth outer skin portion 514. The modified second medical template 201 is arranged such that a central longitudinal part aligns with the midline of the forehead of the user, because this alignment is crucial for proper placement of the associated device during surgery.

The marks on the modified second medical template 201 are visible during planning, and correspond to one or more key anatomical landmarks or positions for electrode placement.

Figure 4B:
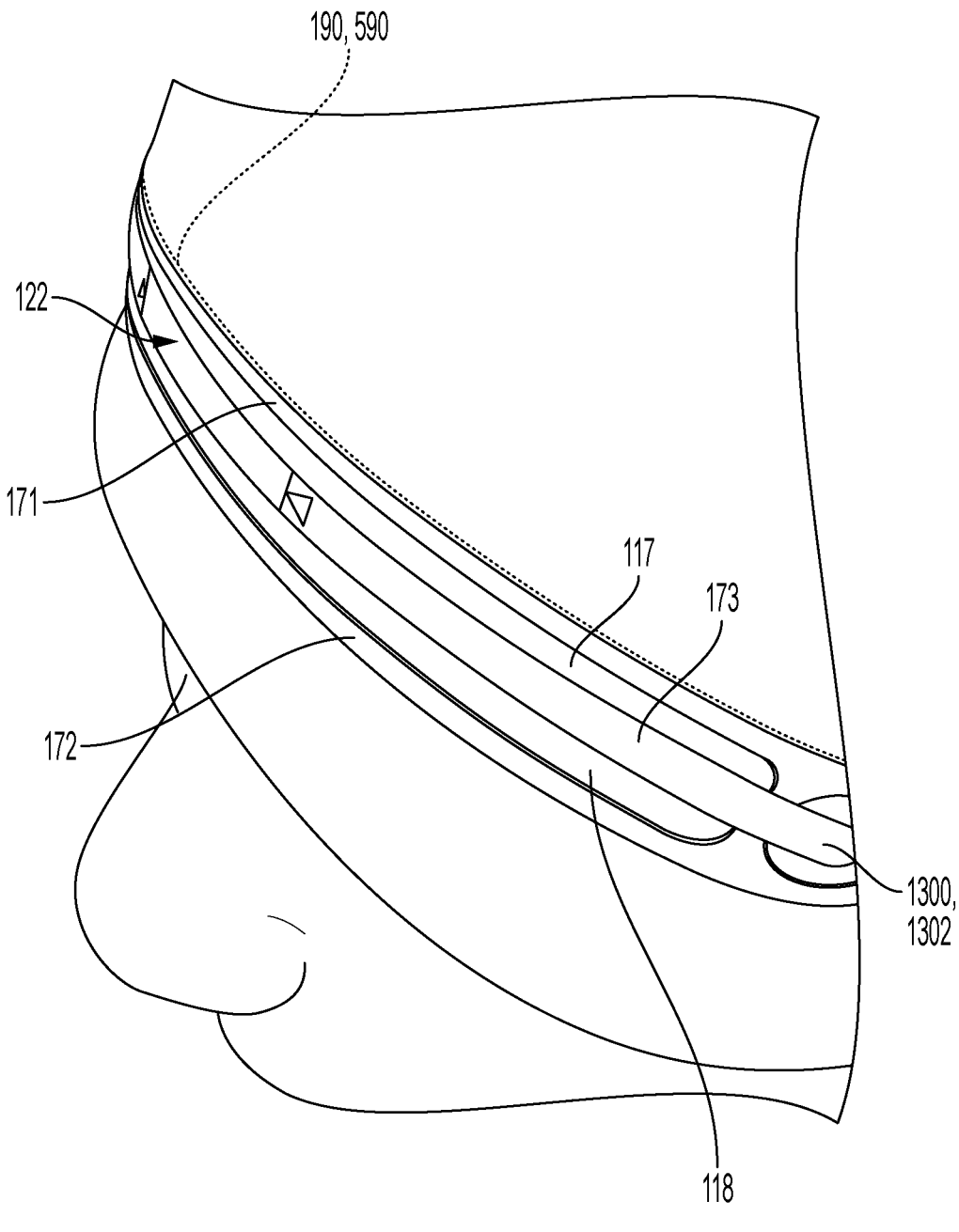
FIG. 4B is a side-angle upper view of a correctly-placed template.

FIG. 4B depicts a side-angled upper view of the modified second medical template (not labelled) after correct placement. The side-angle upper view is the perspective that a planner sees if looking slightly from above at the left-side of the forehead of the user, or the view that a user sees if looking in suitably-arranged mirrors or in a suitably-oriented self-portrait during self-planning. The modified second medical template 201 is positioned approximately horizontally across the forehead of the mannequin in the same placement as depicted in FIG. 4A.

The first template face (not visible) is arranged to be placed adjacent to one or more outer skin portions during planning, wherein the one or more outer skin portions are at least partially comprised in a curved skin plane 590. Skin portions are usually not completely flat, and are often curved or very curved, such as on a portion a head or skull. The first template face is arranged to extend longitudinally along the longitudinal axis (not labelled), and to allow longitudinal curvature such that the first template face is mostly longitudinally comprised in a curved template plane 190. In the example depicted in FIG. 4B, the second template face 122 is be arranged to be visible during planning, and is provided with one or more marks, markings and/or labels.

In the example depicted in FIG. 4B, the one or more elastic cords (not depicted) are arranged to increase the area of the first template face comprised in the curved template plane 190 by applying force to increase the level of conformance between the substrate of the modified second medical template and the curved skin plane 590.

In the example depicted in FIG. 4B, the first template face is arranged to extend transversally along a first transverse axis (not labelled), and to resist transverse curvature such that the first template face is transversely partially comprised in the curved template plane 190. The curved template plane 190 is arranged to be parallel to the curved skin plane 590 during planning. In the example depicted in FIG. 4B, the modified second medical template comprises two grooves 117, 118, extending longitudinally over at least a portion of the third template part (not labelled) and at least a portion of the fourth template part (not labelled), whereby the substrate is separated into two or more longitudinal strips. During planning, if the first template face does not fully conform to the curve skin plane 590, the two or more longitudinal strips provide a degree of mechanical resistance such that one or more portions of each longitudinal strip can deviate to a different amount from the curved template plane 190.

In the example depicted in FIG. 4B, the modified second medical template comprises a first guard rail groove 117 adjacent to a first transverse edge (not labelled) of the modified second medical template, and a second guard rail groove 118 adjacent to a second transverse edge (not labelled) of the modified second medical template. The first guard rail groove 117 and the second guard rail groove 118 extend longitudinally over at least a portion of the third template part and over at least a portion of the fourth template part. The substrate is therefore separated into three longitudinal strips—a first guard rail (not labelled), a central substrate portion (not labelled) and a second guard rail (not labelled).

In the example depicted in FIG. 4B, the first guard rail comprises a first indicator region 171, the second guard rail comprises a second indicator region 172, and the central substrate portion comprises a third indicator region 173. In the example depicted in FIG. 4B, the modified second template is arranged such that, during planning, if the first template face does not fully conform to a curve skin plane 590, the one or more of the three longitudinal strips provide a degree of mechanical resistance such that one or more indicator regions 171, 172, 173 visibly deviate from the curved template plane 190, thereby alerting the planner that the template is not quite flat in the first transverse direction (not labelled). These indicator regions 171, 172, 173 are therefore configured to identify portions where the modified second medical template has buckled, and these portions directly correspond to portions of the associated device which should remain straight flat during placement in a subsequent procedure.

In the example depicted in FIG. 4B, the modified second medical template is correctly-placed, and therefore no buckling can be identified. The close-up view shows the modified second medical template closely conforming to the curvature of the forehead. The modified second medical template is arranged to remains in a fixed position, with no visible signs of slipping or misalignment. Visible deviation of the one or more indicator regions 171, 172, 173 from the curved template plane 190 are very small.

Figure 4C:
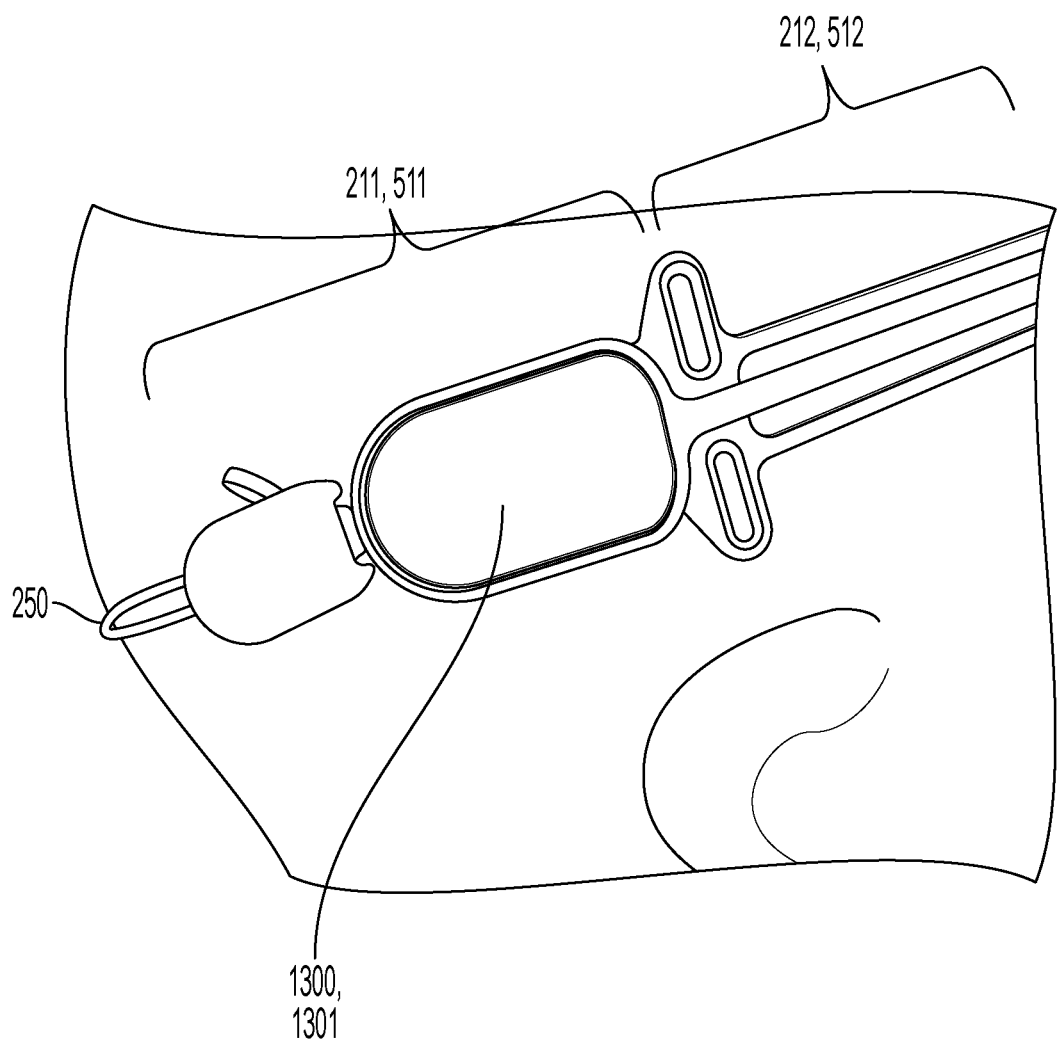
FIG. 4C a right side-view of a correctly-placed template.

FIG. 4C depicts a right-side view of the modified second medical template (not labelled) after correct placement. The right-side view is the perspective that a planner sees if looking at the right ear of the user, or the view that a user sees if looking in suitably-arranged mirrors or in a suitably-oriented self-portrait during self-planning. In the example depicted in FIG. 4C, the modified second medical template is positioned approximately horizontally across the forehead of the mannequin in the same placement as depicted in FIG. 4A & FIG. 4B. In the example depicted in FIG. 4C, the modified second medical template is positioned such that the first template portion 211 is adjacent to the first outer skin portion 511, and the second template portion 212 is adjacent to the second outer skin portion 512. In the example depicted in FIG. 4C, the second outer skin portion 512 comprises a portion of the right temporal region of the user.

In the example depicted in FIG. 4C, the modified second medical template is securely held in place by one or more elastic cords 250.

Figure 4D:
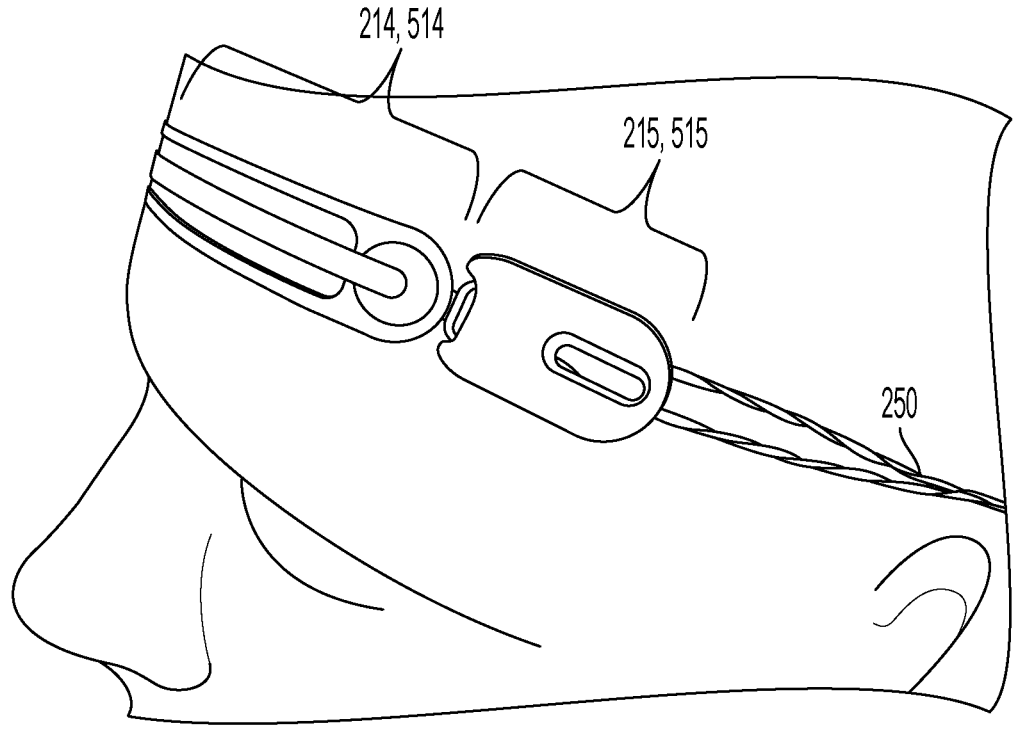
FIG. 4D a left-front view of a correctly-placed template.

FIG. 4D depicts a front-left view of the modified second medical template (not labelled) after correct placement. The front-left view is the perspective that a planner sees if looking at the left temple region of the user, or the view that a user sees if looking in suitably-arranged mirrors or in a suitably-oriented self-portrait during self-planning. In the example depicted in FIG. 4D, the modified second medical template is positioned approximately horizontally across the forehead of the mannequin in the same placement as depicted in FIG. 4A, 4B & FIG. 4C. In the example depicted in FIG. 4D, the modified second medical template is positioned such that the fourth template portion 214 is adjacent to the fourth outer skin portion 514, and the fifth template portion 215 is adjacent to the fifth outer skin portion 515. In the example depicted in FIG. 4D, the fourth outer skin portion 514 comprises a portion of the forehead of the user, and the fifth outer skin portion 515 comprises a portion of the left temporal region of the user.

In the example depicted in FIG. 4D, the modified second medical template is securely held in place by one or more elastic cords 250.

Figure 5A:
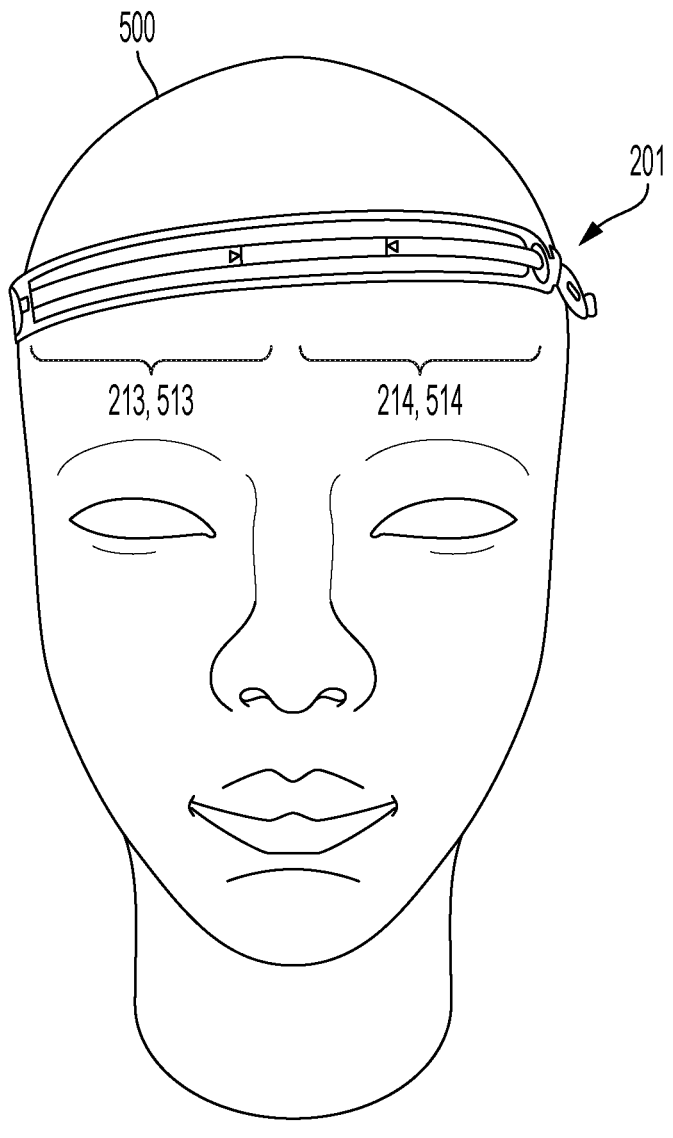
FIG. 5A is a front-view of an incorrectly-placed template.
Figure 5B:
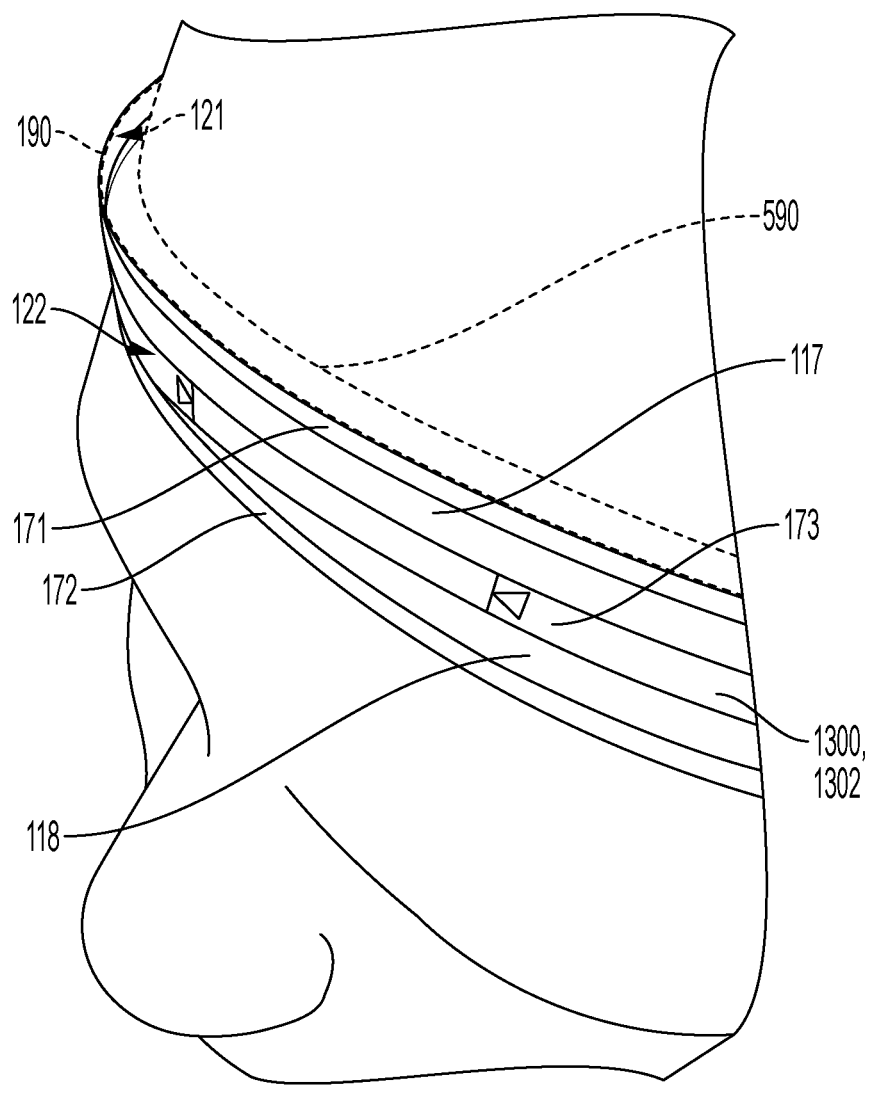
FIG. 5B is a side-angled view of an incorrectly-placed template.

FIGS. 5A to 5B collectively depict different views of an incorrectly-placed medical template as described herein. In these examples, the modified second medical template 201 as depicted in FIG. 3, and as depicted in FIG. 4A to 4D, is arranged to be incorrectly-placed on one or more body-parts 500 of a user. In these examples, the one or more body-parts 500 are approximately the same as those depicted in FIG. 4A to 4D.

In these examples, the associated device (not depicted) is the same as described above in relation to FIG. 4A to 4D.

FIG. 5A depicts a front-view of the modified second medical template 201 after incorrect placement. The front-view is the same perspective as in FIG. 4A, but in the example depicted in FIG. 5A, the modified second medical template 201 is positioned across the forehead of the mannequin, but not approximately horizontally. The modified second medical template 201 should be positioned lower on the forehead, towards the chin of the user and closer to the brow line. In the example depicted in FIG. 5A, the modified second medical template 201 is arranged such that a central longitudinal part aligns with the midline of the forehead of the user.

In the example depicted in FIG. 5A, the third template portion 213 is placed approximately adjacent to the third outer skin portion 513, similar to FIG. 4A, but slightly higher towards the top of the head. The example depicted in FIG. 5A differs from FIG. 4A by the fourth template portion 214 being placed higher above the fourth outer skin portion 514. If this placement is followed for the associated device, there is a risk that the device portion corresponding to the fourth template portion 214 will be incorrectly placed.

Such an incorrect placement can cause the associated device to fail and/or operate incorrectly. If the associated device is a neurostimulator, such an incorrect placement can cause inaccuracies in electrode positioning. If the associated device is at least partially implanted, such an incorrect placement can cause inaccuracies in implant positioning, affecting the efficacy of any surgical steps in any subsequent procedure.

Such an incorrect placement can cause portions of the associated device to be twisted and/or buckled. Such an incorrect placement can cause placement problems which must be resolved in any subsequent procedure, such as surgery.

The modified second medical template 201 comprises one or more elastic cords (not depicted), arranged to remain in position after placement.

In the example depicted in FIG. 5A, incorrect placement has been exaggerated to ensure that the deviations are visible in these photographs. In practice, incorrect placements are expected to be smaller, but still visible to a planner using a medical template as described herein.

FIG. 5B depicts a side-angled upper view of the modified second medical template (not labelled) after incorrect placement. The side-angled upper view is the same perspective as in FIG. 4B, but in the example depicted in FIG. 5B, the modified second medical template 201 is positioned across the forehead of the mannequin, but not approximately horizontally. The modified second medical template 201 should be positioned lower on the forehead, towards the chin of the user and closer to the brow line.

The modified second medical template 201 depicted in FIG. 5A is positioned in the same placement as depicted in FIG. 5A. The one or more body-parts are the same as the one or more body parts depicted in FIG. 5A. In the example depicted in FIG. 5B, the one or more outer skin portions are at least partially comprised in a curved skin plane 590.

The first template face 121 is arranged to be placed adjacent to one or more outer skin portions during planning. The first template face 121 is arranged to extend longitudinally along the longitudinal axis (not labelled), and to allow longitudinal curvature such that the first template face 121 is mostly longitudinally comprised in a curved template plane 190.

In the example depicted in FIG. 5B, the one or more elastic cords (not depicted) are arranged to increase the area of the first template face 121 comprised in the curved template plane 190 by applying force to increase the level of conformance between the substrate of the modified second medical template and the curved skin plane 590.

In the example depicted in FIG. 5B, the first template face 121 is arranged to extend transversally along a first transverse axis (not labelled), and to resist transverse curvature such that the first template face 121 is transversely partially comprised in the curved template plane 190. The curved template plane 190 is arranged to be parallel to the curved skin plane 590 during planning. In the example depicted in FIG. 5B, the modified second medical template comprises two grooves 117, 118, extending longitudinally over at least a portion of the third template part (not labelled) and at least a portion of the fourth template part (not labelled), whereby the substrate is separated into two or more longitudinal strips. In the example depicted in FIG. 5B, the first template face 121 does not fully conform to the curve skin plane 590, the two or more longitudinal strips provide a degree of mechanical resistance such that one or more portions of each longitudinal strip can deviate to a different amount from the curved template plane 190.

In the example depicted in FIG. 5B, the modified second medical template comprises a first guard rail groove 117 adjacent to a first transverse edge (not labelled) of the modified second medical template, and a second guard rail groove 118 adjacent to a second transverse edge (not labelled) of the modified second medical template. The first guard rail groove 117 and the second guard rail groove 118 extend longitudinally over at least a portion of the third template part and over at least a portion of the fourth template part. The substrate is therefore separated into three longitudinal strips—a first guard rail (not labelled), a central substrate portion (not labelled) and a second guard rail (not labelled). In the example depicted in FIG. 5B, the first guard rail comprises a first indicator region 171, the second guard rail comprises a second indicator region 172, and the central substrate portion comprises a third indicator region 173.

In the example depicted in FIG. 5B, the modified second template is arranged such that, during planning, if the first template face 121 does not fully conform to a curve skin plane 590, the one or more of the three longitudinal strips provide a degree of mechanical resistance such that one or more indicator regions 171, 172, 173 visibly deviate from the curved template plane 190, thereby alerting the planner that the template is not quite flat in the first transverse direction (not labelled). These indicator regions 171, 172, 173 are therefore configured to identify portions where the modified second medical template has buckled, and these portions directly correspond to portions of the associated device which should remain straight flat during placement in a subsequent procedure.

In the example depicted in FIG. 5B, the modified second medical template is incorrectly-placed, and therefore buckling can be visibly identified. The close-up view shows the modified second medical template deviating from the curvature of the forehead.

The modified second medical template is arranged to remain in a fixed position, but in the example depicted in FIG. 5B with visible signs of slipping or misalignment. The visible deviations of the one or more indicator regions 171, 172, 173 from the curved template plane 190 are very large.

Such visible indications allows a planner to easily identify and correct the incorrect placement of the modified second medical template. A planner can easily ensure that the placement of the modified medical template is more correct, approaching the situation depicted in FIG. 4A to 4D. This means that the risk of negative consequences during any subsequent procedures are greatly reduced.

Figure 6:
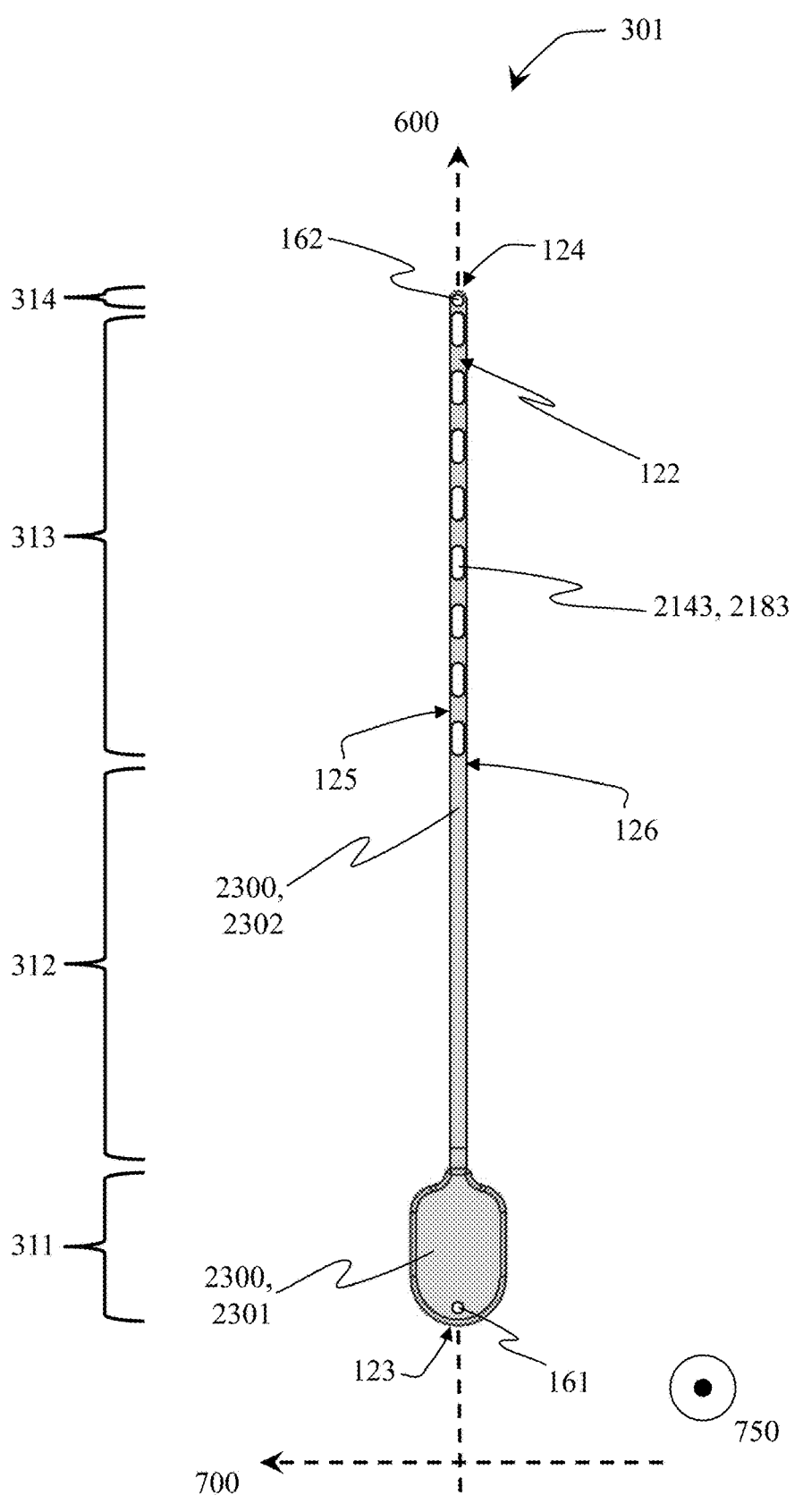
FIG. 6 is a further embodiment of a medical template.

FIG. 6 depicts a third embodiment of a medical template 301 (or a third medical template) suitable for planning a subsequent procedure such as a placement of one or more device portions, wherein the one or more device portions are arranged to be at least partially implantable subcutaneously in one or more body parts (not depicted). The subsequent procedure can include one or more cosmetic and/or medical steps.

As depicted in FIG. 6, the third medical template 301 comprises: a substrate extending along a longitudinal axis 600 and further extending along a first transverse axis 700; one or more template portions 311, 312, 313, 314; and one or more further alignment marks 2143, 2183.

In the example depicted in FIG. 6, the third medical template 301 optionally comprises a first template portion 311, a second template portion 312, a third template portion 313 and a fourth template portion 314, arranged adjacently along the longitudinal axis 600. The first template portion 311 is arranged at a proximal end (not labelled) of the third medical template 301. The fourth template portion 314 is arranged at a distal end (not labelled) of the third medical template 301.

Similar to the first medical template 101 and the second medical template 201 described above, the one or more template portions 311, 312, 313, 314 of the third medical template 301 comprise a first template face (not depicted) arranged to be placed adjacent to one or more outer skin portions (not depicted) of the user. Optionally, the one or more template portions 311, 312, 313, 314 can comprise a second template face 122, on the opposite side of the substrate to the first template face. Optionally, the second template face 122 can comprise one or more marks, markers and/or labels.

The third medical template 301 as depicted in FIG. 6 differs from the first medical template 101 and the second medical template 201 by arranging the second template face 122 to be at least partially visible during planning.

The third medical template 301 as depicted in FIG. 6 differs from the first medical template 101 and the second medical template 201 by comprising one or more further alignment marks 2143, 2183 arranged to indicate one or more alignment axes and/or tolerances of placement.

Optionally, one or more positions and/or one or more extents of the one or more offset alignment marks can be offset to a degree corresponding to an implantation depth of a corresponding portion of the one or more device portions. In the example depicted in FIG. 6, one or more positions and/or one or more extents of the one or more further alignment marks 2143, 2183 can be arranged to be offset in one or more longitudinal directions 600, in one or more transverse directions 700, or any combination thereof. For example, one or more extents of the third medical template 301 can be scaled in the longitudinal direction 600 to anticipate an average thickness of skin, a specific thickness of skin, an average implantation depth, a specific implantation depth, or any combination thereof. For example, if the first template face 121 is arranged to extend longitudinally 600, and to allow longitudinal curvature such that the first template face 121 is mostly longitudinally comprised in a curved template plane 190, one or more longitudinal extents can be made larger or longer.

Any suitable method for determining one or more offsets can be used, including trial and error, simulation, approximation, measurement, estimation, or any combination thereof. Anatomical data can be used based upon, for example, anatomical measurement of an individual, anatomical measurement of a population, an entry in an anatomical database, or any combination thereof. For example, if the third medical template 301 is arranged to be placed against one or more curved outer skin portions, one or more estimations of average circumference and curvature can be used. For example, if one or more outer skin portions are comprised in a head, one or more outer skin portions are at least partially comprised in a curved skin plane. For example, such a curved surface plane can be approximated to a circle. For example, an average head circumference of an adult human can be in the range of 35 cm to 80 cm, in the range of 40 cm to 75 cm, or in the range 47 cm to 66 cm, or approximately 50 cm. For example, a suitable offset can be calculated corresponding to an extra length of a medical template as 2n (2.pi)×an average implantation depth.

For example, an average skin thickness of a human head of a Caucasian female, aged 60 years, can be in the range 2.5 mm+/−0.9 mm, with thinner values over frontal and occipital lobes, based on "Measuring tissue thicknesses of the human head using centralized and normalized trajectories" in 2009 by Wendel-Mitoraj, Katrina & Stoliar, Dmytro & Malmivuo, Jaakko & Hyttinen, Jari, found at: https://www.researchgate.net/publication/254257562_Measuring_tissue_thicknesses_of_the_human_head_using_centralized_and_normalized_trajectories. For example, an average skin thickness can be used to estimate a minimum implantation depth of approx. 1.6 mm to 3.4 mm.

Additionally or alternatively, an average implantation depth of an associated device for neurostimulation can be estimated to be the range of 3 mm to 12 mm, with approximately 6 mm being typical.

For example, if the third medical template 301 is arranged for planning a placement of an associated device for supra-orbital nerve stimulation (SONS), the associated SONS device can have a total longitudinal length of approximately 25 cm. If an average head circumference is assumed to be 50 cm, the associated SONS device extends approximately ½ of an average head circumference. If an average implantation depth is assumed to be 6 mm, then an offset in the corresponding total longitudinal length of the third medical template 301 can be estimated as: 2n (2.pi)×6 mm×½=approximately 18.85 mm longer.

Similar to the first medical template 101 and the second medical template 201 described above, the third medical template 301 can optionally comprise a dummy device of the associated device (dummy device) to reduce the risk of inconsistencies between the dimensions and markings of the third medical template 301 and the associated device.

The third medical template 301 as depicted in FIG. 6 differs from the first medical template 101 and the second medical template 201 by optionally comprising a further dummy device 2300 of the associated device, wherein the further dummy device 2300 optionally comprises one or more offsets. The optional one or more offsets are arranged to reduce the risk of inconsistencies between the dimensions and markings of the third medical template 301 and the associated device after implantation. The further dummy device 2300 optionally comprises one or more positions and/or one or more extents offset to a degree corresponding to an implantation depth of a corresponding portion of the one or more device portions. If the associated device is, for example, a neurostimulator, the further dummy device 2300 can comprise a further dummy pulse generator 2301 and/or one or more further dummy electrodes 2302. The one or more further dummy electrodes 2302 can represent the foil or conductor component of the associated device, assisting in the alignment of the one or more conductive elements. In the example depicted in FIG. 6, the third medical template 301 optionally comprises one or more further dummy electrodes 2302 with one or more further longitudinal alignment marks 2143. The one or more further longitudinal alignment marks 2143 can optionally comprise one or more offsets corresponding to an implantation depth of a corresponding portion of the one or more device portions. In the example depicted in FIG. 6, the third medical template 301 optionally comprises one or more further transverse alignment marks 2183. The one or more further transverse alignment marks 2183 can optionally comprise one or more offsets corresponding to an implantation depth of a corresponding portion of the one or more device portions. For example, the further dummy device 2300 depicted in FIG. 6 can be arranged to have an additional longitudinal extent or a positive longitudinal offset along the longitudinal axis 600 than the associated device to compensate for an average implant depth. For example, a positive longitudinal extent can be in the range of approximately 5% to 20%, 5% to 10%, or approximately 7.5%. The one or more further alignment marks 2143, 2183 can be arranged to indicate one or more offset positions and/or one or more offset extents of the one or more electrodes comprised in the associated device, allowing a planner to accurately determine correct positions for the one or more electrodes to be implanted subcutaneously.

In the example depicted in FIG. 6, the first template portion 311 extends from the proximal end of the third medical template 301 to an optional second template portion 312 comprising no offset alignment marks. In the example depicted in FIG. 6, the third template portion 313 comprises one or more further alignment marks 2143, 2183. An offset transverse alignment mark 2183 extends transversely approximately parallel to the first transverse axis 700. The offset transverse alignment mark 2183 provides a suitable means to allow the planner to mark one or more outer skin portions of the user with one or more positions of the offset transverse alignment mark 2183, thereby marking one or more outer skin portions with one or more positions and/or one or more extents corresponding to an implantation position of one or more corresponding device portions.

In the example depicted in FIG. 6, the third template portion 313 extends from the optional second template portion 312 to the fourth template portion 314. In the example depicted in FIG. 6, the fourth template portion 314 extends from the third template portion 313 to the distal end of the third medical template 301.

Similar to the first medical template 101 and the second medical template 201 described above, the first template face of the third medical template 301 is arranged to be placed adjacent to one or more outer skin portions during planning, wherein the one or more outer skin portions are at least partially comprised in a curved skin plane. The first template face is arranged to extend longitudinally along the longitudinal axis 600, and to allow longitudinal curvature such that the first template face is mostly longitudinally comprised in a curved template plane. The first template face is further arranged to extend transversally along the first transverse axis 700.

Optionally, the third medical template 301 can be arranged similar to the first medical template 101 and the second medical template 201, whereby the first template face can be further arranged to resist transverse curvature such that the first template face is transversely partially comprised in the curved template plane.

Optionally, the third medical template 301 can be arranged similar to the first medical template 101 and the second medical template 201, to comprise one or more mechanically-resistive regions arranged to mechanically resist transverse curvature of the first template face such that at least a portion of the one or more mechanically-resistive regions deviates from the curved template plane.

Optionally, the third medical template 301 can be arranged similar to the first medical template 101 and the second medical template 201, to comprises one or more guard rail grooves and/or one or more guard rails. Optionally, the one or more guard rails can comprise one or more indicator regions.

Similar to the first medical template 101 and the second medical template 201 described above, the third medical template 301 can optionally comprise one or more attachment positions 161, 162, and the third medical template 101 can further comprise one or more cords and/or ties attached to the one or more attachment positions 161, 162.

Similar to the first medical template 101 and the second medical template 201 described above, the third medical template 301 can optionally comprise can optionally comprise one or more marking grooves, arranged to be large enough to allow a marker to pass through. Optionally, one or more marks, markings and/or labels can be provided on the third medical template 301 to guide the planner to align the third medical template 301 correctly with respect to one or more anatomical features of the one or more body parts. Optionally, one or more marks, markings and/or labels can be provided on the second template face 122. Optionally, one or more marks, markings and/or labels can be provided with a suitable offset. Optionally, shading and/or color coding can be used to distinguish the functions of different parts and/or markings. Optionally, one or more areas can be provided for branding and/or critical instructions, such as a visible surface of the offset dummy pulse generator 2301. Optionally, the third medical template 301 can comprise one or more bumper areas or bumper regions. Optionally, the third medical template 301 can comprise one or more tolerance marks.

Figure 7:
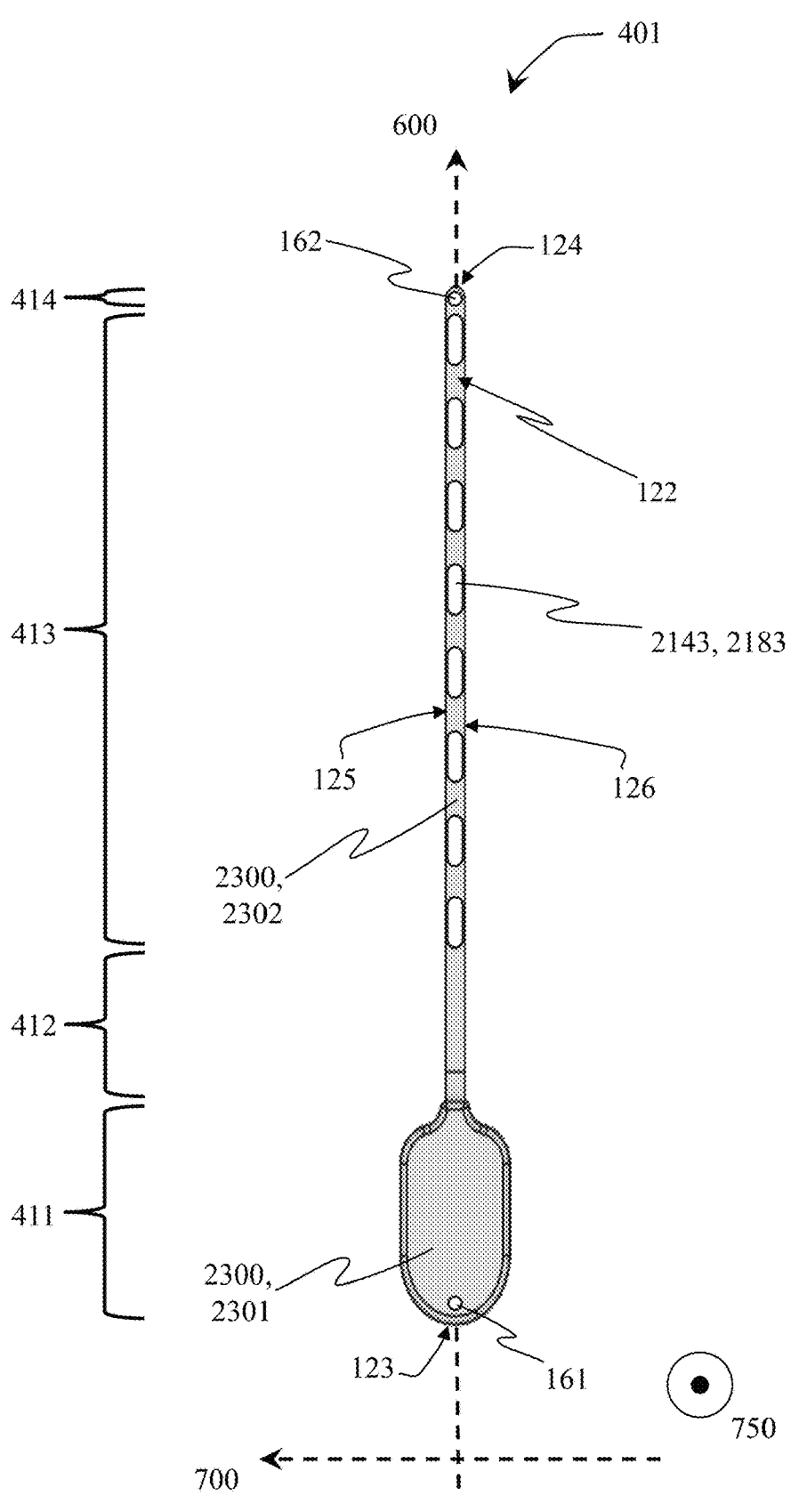
FIG. 7 is a further embodiment of a medical template.

FIG. 7 depicts a fourth embodiment of a medical template 401 (or a fourth medical template) suitable for planning a subsequent procedure such as a placement of one or more device portions, wherein the one or more device portions are arranged to be at least partially implantable subcutaneously in one or more body parts (not depicted). The subsequent procedure can include one or more cosmetic and/or medical steps.

As depicted in FIG. 7, the fourth medical template 401 comprises: a substrate extending along a longitudinal axis 600 and further extending along a first transverse axis 700; one or more template portions 411, 412, 413, 414; and one or more further alignment marks 2143, 2183.

In the example depicted in FIG. 7, the fourth medical template 401 optionally comprises a first template portion 411, a second template portion 412, a third template portion 413 and a fourth template portion 414, arranged adjacently along the longitudinal axis 600. The first template portion 411 is arranged at a proximal end (not labelled) of the fourth medical template 401. The fourth template portion 414 is arranged at a distal end (not labelled) of the fourth medical template 401.

Similar to the third medical template 301 described above, the one or more template portions 411, 412, 413, 414 of the fourth medical template 401 comprise a first template face (not depicted) arranged to be placed adjacent to one or more outer skin portions (not depicted) of the user. Optionally, the one or more template portions 411, 412, 413, 414 can comprise a second template face 122, on the opposite side of the substrate to the first template face. Optionally, the second template face 122 can comprise one or more marks, markers and/or labels.

The fourth medical template 401 as depicted in FIG. 7 differs from the third medical template 301 by comprising a second template portion 412 with a smaller longitudinal extent along the longitudinal axis 600 than the second template portion 312 of the third medical template 301.

Similar to the third medical template 301, one or more positions and/or one or more extents of the one or more further alignment marks 2143, 2183 of the fourth medical template 401 can be arranged to be offset in one or more longitudinal directions 600, in one or more transverse directions 700, or any combination thereof.

Similar to the third medical template 301, one or more extents of the fourth medical template 301 can be scaled in the longitudinal direction 600 to anticipate an average thickness of skin, a specific thickness of skin, an average implantation depth, a specific implantation depth, or any combination thereof. For example, if the first template face 121 is arranged to extend longitudinally 600, and to allow longitudinal curvature such that the first template face 121 is mostly longitudinally comprised in a curved template plane 190, one or more longitudinal extents can be made larger or longer.

For example, if the fourth medical template 401 is arranged for planning a placement of an associated device for occipital nerve stimulation (ONS), the associated ONS device can have a total longitudinal length of approximately 17 cm. If an average head circumference is assumed to be 51 cm, the associated ONS device extends approximately ⅓ of an average head circumference. If an average implantation depth is assumed to be 6 mm, then an offset in the corresponding total longitudinal length of the fourth medical template 401 can be estimated as: 2n (2.pi)×6 mm×⅓=approximately 12.57 mm longer.

Similar to the third medical template 301, the further dummy device 2300 depicted in FIG. 7 can be arranged to have an additional longitudinal extent or a positive longitudinal offset along the longitudinal axis 600 than the associated device to compensate for an average implant depth. For example, a positive longitudinal extent can be in the range of approximately 58 to 208, 5% to 10%, or approximately 7.5%. The one or more further alignment marks 2143, 2183 can be arranged to indicate one or more offset positions and/or one or more offset extents of the one or more electrodes comprised in the associated device, allowing a planner to accurately determine correct positions for the one or more electrodes to be implanted subcutaneously.

In summary, medical templates are often used to mark the skin when planning a subsequent procedure, but they can be tedious to use. Placement & fixation by one person is difficult, placement and incision tolerances are unclear and incorrect. So, a medical template is provided comprising one or more template portions corresponding to one or more device portions, with a first template face 121, arranged to be placed adjacent to one or more outer skin portions at least partially comprised in a curved skin plane 590; the first template face 121 being arranged to extend & curve longitudinally in a curved template plane 190, wherein the curved template plane 190 is arranged to be parallel to the curved skin plane 590. The medical template can comprise mechanically-resistive regions 130 arranged to resist transverse curvature of the first template face 121 such that at least a portion of the one or more mechanically-resistive regions deviates from the curved template plane 590. The medical template can also comprise one or more alignment marks 143, 183 offset to a degree corresponding to an implantation depth of a corresponding portion of the one or more device portions.

REFERENCE NUMBERS

101: first medical template
111: first template portion
112: second template portion
113: third template portion
114: fourth template portion
116: bumper area or bumper region
117: first guard rail groove
118: second guard rail groove
121: first template face
122: second template face
123: first longitudinal edge
124: second longitudinal edge
125: first transverse edge
126: second transverse edge
143: longitudinal alignment mark
145: longitudinal tolerance mark
161: first attachment position
162: second attachment position
171: first indicator region
172: second indicator region
173: third indicator region
183: transverse alignment mark
186: transverse incision mark
190: curved template plane
201: second medical template
211: first template portion
212: second template portion
213: third template portion
214: fourth template portion
215: fifth template portion
246: longitudinal incision mark
250: elastic cord
301: third medical template
311: first template portion
312: second template portion
313: third template portion
314: fourth template portion
401: fourth medical template
411: first template portion
412: second template portion
413: third template portion
414: fourth template portion
500: body part

24

511: first outer skin portion
512: second outer skin portion
513: third outer skin portion
514: fourth outer skin portion
515: fifth outer skin portion
590: curved skin plane
600: longitudinal axis
700: first transverse axis
750: second transverse axis
1300: dummy of associated device
1301: dummy pulse generator
1302: dummy stimulation electrodes
2300: further dummy of associated device
2301: further dummy pulse generator
2302: further dummy stimulation electrodes
2143: further longitudinal alignment mark
2183: further transverse alignment mark.

The invention claimed is:

1. A medical template for planning a placement of one or more device portions, wherein the one or more device portions are comprised in an associated device for neuro-stimulation,
    wherein the one or more device portions are arranged to be at least partially implantable subcutaneously,
        wherein the medical template comprises:
        one or more template portions corresponding to the one or more device portions, the one or more template portions comprising a first template face, arranged to be placed adjacent to one or more outer skin portions of one or more body parts;
        wherein the one or more outer skin portions are at least partially comprised in a curved skin plane;
        wherein the first template face is arranged to extend longitudinally and to allow longitudinal curvature such that the first template face is mostly longitudinally comprised in a curved template plane;
        wherein the curved template plane is arranged to be parallel to the curved skin plane;
    wherein the medical template further comprises one or more alignment marks arranged to indicate one or more alignment axes and/or tolerances of placement; and
    wherein one or more positions and/or one or more extents of the one or more alignment marks is offset with respect to the one or more outer skin portions by a first distance that corresponds to an implantation depth of a corresponding portion of the one or more device portions.

2. The medical template according to claim 1, wherein the first distance is in one or more directions along the first surface, wherein the one or more directions are selected from the group consisting of: one or more longitudinal directions, one or more transverse directions, or any combination thereof.

3. The medical template according to claim 1, wherein the medical template is a surgical template.

4. The medical template according to claim 1, further comprising one or more incision marks, arranged to indicate one or more incision points and/or arranged to indicate one or more tolerances of incision.

5. The medical template according to claim 1, further comprising one or more incision marks, arranged to indicate one or more suitable directions for one or more incisions.

6. The medical template according to claim 1, wherein the one or more body parts comprise at least a portion of a head, of a forehead, of a brow, of a temple region, or any combination thereof.

7. The medical template according to claim 1, wherein the first template face is arranged to resist transverse curvature such that the first template face is transversely partially comprised in the curved template plane;

wherein the medical template further comprises one or more mechanically-resistive regions arranged to mechanically resist transverse curvature of the first template face such that at least a portion of the one or more mechanically-resistive regions deviates from the curved template plane when the first template face does not fully conform to a curve skin plane.

8. The medical template according to claim 1, further comprising one or more indicator regions, arranged to indicate one or more deviations of the first template face from the curved template plane.

9. The medical template according to claim 8, wherein the one or more indicator regions are arranged to indicate one or more deviations of the first template face in one or more longitudinal curvatures, in one or more transverse curvatures, or any combination thereof.

10. The medical template according to claim 8, wherein the one or more indicator regions are provided adjacent to a longitudinal edge, adjacent to a transverse edge, or any combination thereof.

11. The medical template according to claim 10, wherein the one or more indicator regions are configured to show when the medical template deviates from a predetermined plane in which the medical template is placed adjacent to the one or more outer skin portions of the one or more body parts.

12. The medical template according to claim 11, wherein the deviation comprises (i) being improperly flat against the one or more outer skin portions, and/or (ii) buckling.

13. The medical template according to claim 1, further comprising one or more attachment positions, and further comprising one or more elastic cords attached to the one or more attachment positions, wherein the one or more elastic cords are arranged to increase the area of the first template face comprised in the curved template plane.

14. The medical template according to claim 13, wherein the one or more elastic cords are arranged to retain the medical template against at least a portion of the one or more body parts.

15. The medical template according to claim 13, wherein the one or more elastic cords are arranged to allow placement by one person.

16. The medical template according to claim 1, further comprising one or more guard rail grooves, arranged to assist in drawing one or more planning lines on one or more outer skin portions.

17. The medical template according to claim 16, wherein the one or more guard rail grooves are disposed adjacent to one or more edges of the medical template.

18. The medical template according to claim 1, further comprising one or more bumper regions, arranged to indicate that the one or more bumper regions are to be kept free to reduce risk of interference with one or more further associated devices to be placed.

19. The medical template according to claim 18, wherein the one or more bumper regions are disposed at one or more ends of the medical template.

20. The medical template according to claim 1, further comprising one or more magnets, arranged to test a placement compatibility with one or more peripherals arranged to be attached to the associated device.

21. The medical template according to claim 1, the one or more device portions comprising one or more portions of a cardboard, a printed cardboard, a plastic, or any combination thereof.

22. The medical template according to claim 1, further comprising a dummy device of the associated device, wherein the dummy device comprises one or more positions, one or more extents, one or more marks, or any combination thereof, corresponding to a portion of the one or more device portions.

23. The medical template according to claim 22, wherein the dummy device comprises one or more positions and/or one or more extents offset to a degree corresponding to an implantation depth of a corresponding portion of the one or more device portions.

24. The medical template according to claim 1, wherein the one or more alignment marks are configured to indicate one or more reference points on the one or more outer skin portions for marking and making incisions thereon.

* * * * *